US011384208B2

(12) United States Patent
Lee et al.

(10) Patent No.: US 11,384,208 B2
(45) Date of Patent: *Jul. 12, 2022

(54) SUPER ABSORBENT POLYMER AND METHOD FOR PRODUCING SAME

(71) Applicant: LG Chem, Ltd., Seoul (KR)

(72) Inventors: Sang Gi Lee, Daejeon (KR); Hye Mi Nam, Daejeon (KR); Soo Jin Lee, Daejeon (KR); Chang Sun Han, Daejeon (KR); Moo Kon Kim, Daejeon (KR)

(73) Assignee: LG Chem, Ltd.

( * ) Notice: Subject to any disclaimer, the term of this patent is extended or adjusted under 35 U.S.C. 154(b) by 709 days.

This patent is subject to a terminal disclaimer.

(21) Appl. No.: 16/085,406

(22) PCT Filed: May 10, 2017

(86) PCT No.: PCT/KR2017/004832
§ 371 (c)(1),
(2) Date: Sep. 14, 2018

(87) PCT Pub. No.: WO2018/124404
PCT Pub. Date: Jul. 5, 2018

(65) Prior Publication Data
US 2019/0077924 A1 Mar. 14, 2019

(30) Foreign Application Priority Data

Dec. 27, 2016 (KR) .................. 10-2016-0180348
Apr. 19, 2017 (KR) .................. 10-2017-0050399

(51) Int. Cl.
| | |
|---|---|
| *C08J 3/075* | (2006.01) |
| *C08J 3/24* | (2006.01) |
| *C08J 9/08* | (2006.01) |
| *B01J 20/26* | (2006.01) |
| *B01J 20/28* | (2006.01) |
| *C08F 2/06* | (2006.01) |
| *A61L 15/60* | (2006.01) |
| *C08F 2/44* | (2006.01) |
| *C08J 3/12* | (2006.01) |
| *C08F 6/00* | (2006.01) |

(52) U.S. Cl.
CPC .............. *C08J 3/075* (2013.01); *A61L 15/60* (2013.01); *B01J 20/267* (2013.01); *B01J 20/28004* (2013.01); *B01J 20/28016* (2013.01); *C08F 2/06* (2013.01); *C08F 2/44* (2013.01); *C08F 6/008* (2013.01); *C08J 3/12* (2013.01); *C08J 3/24* (2013.01); *C08J 3/245* (2013.01); *C08J 9/08* (2013.01); *B01J 2220/68* (2013.01); *C08J 2203/02* (2013.01); *C08J 2205/022* (2013.01); *C08J 2300/12* (2013.01); *C08J 2333/02* (2013.01)

(58) Field of Classification Search
CPC ................ B01J 20/267; B01J 20/28004; B01J 20/28016; C08J 3/075
See application file for complete search history.

(56) References Cited

U.S. PATENT DOCUMENTS

| | | | |
|---|---|---|---|
| 4,883,478 A | 11/1989 | Lerailler et al. | |
| 7,803,880 B2 * | 9/2010 | Torii ...................... | C08F 20/06 525/329.7 |
| 2005/0070616 A1 | 3/2005 | Champ et al. | |
| 2011/0224361 A1 | 9/2011 | Daniel et al. | |
| 2011/0301027 A1 | 12/2011 | Bitis et al. | |
| 2012/0296297 A1 | 11/2012 | Di Cintio et al. | |
| 2013/0026412 A1 | 1/2013 | Machida et al. | |
| 2014/0306156 A1 | 10/2014 | Tian et al. | |
| 2014/0312273 A1 * | 10/2014 | Wattebled ............... | A61L 15/24 252/194 |
| 2015/0093575 A1 | 4/2015 | Naumann et al. | |
| 2015/0283284 A1 | 10/2015 | Azad et al. | |
| 2016/0318002 A1 | 11/2016 | Lee et al. | |
| 2016/0354757 A1 | 12/2016 | Lee et al. | |
| 2016/0367965 A1 | 12/2016 | Kim et al. | |
| 2017/0014801 A1 | 1/2017 | Ikeuchi et al. | |
| 2018/0050321 A1 * | 2/2018 | Lee ........................ | B01J 20/265 |
| 2018/0056274 A1 | 3/2018 | Lee et al. | |

FOREIGN PATENT DOCUMENTS

| | | | |
|---|---|---|---|
| CN | 102245218 A | 11/2011 | |
| CN | 105916902 A | 8/2016 | |
| CN | 106232235 A | 12/2016 | |
| CN | 107428865 A | 12/2017 | |
| EP | 3098245 A1 | 11/2016 | |
| EP | 3248990 A1 | 11/2017 | |
| EP | 3248991 A1 | 11/2017 | |

(Continued)

OTHER PUBLICATIONS

Chinese Search Report for Application No. CN201780015968.3 dated Jul. 10, 2020.

(Continued)

*Primary Examiner* — Yong L Chu
(74) *Attorney, Agent, or Firm* — Lerner, David, Littenberg, Krumholz & Mentlik, LLP

(57) ABSTRACT

A super absorbent polymer according to the present invention has an excellent discoloration resistance property even under high temperature/high humidity conditions, while maintaining excellent absorption performance, and is preferably used for hygienic materials such as diapers, and thus can exhibit excellent performance.

10 Claims, No Drawings

(56) References Cited

FOREIGN PATENT DOCUMENTS

| | | |
|---|---|---|
| EP | 3248993 A1 | 11/2017 |
| EP | 3249001 A1 | 11/2017 |
| EP | 3260485 A1 | 12/2017 |
| EP | 3312218 A1 | 4/2018 |
| EP | 3318596 A1 | 5/2018 |
| EP | 3342802 A1 | 7/2018 |
| JP | H10130324 A | 5/1998 |
| JP | 2016016667 A | 2/2016 |
| KR | 20040091010 A | 10/2004 |
| KR | 20130093477 A | 8/2013 |
| KR | 20130120300 A | 11/2013 |
| KR | 20130138851 A | 12/2013 |
| KR | 20140102264 A | 8/2014 |
| KR | 20150068322 A | 6/2015 |
| KR | 20150116418 A | 10/2015 |
| KR | 20150140800 A | 12/2015 |
| KR | 20160048838 A | 5/2016 |
| KR | 20160063956 A | 6/2016 |
| KR | 101655104 B1 | 9/2016 |
| KR | 20160127742 A | 11/2016 |
| KR | 20160137499 A | 11/2016 |
| KR | 20160141666 A | 12/2016 |
| KR | 20160148986 A | 12/2016 |
| WO | 8703208 A1 | 6/1987 |
| WO | 2005063313 A1 | 7/2005 |
| WO | 2015163508 A1 | 10/2015 |
| WO | 2016195376 A1 | 12/2016 |
| WO | 2017146347 A1 | 8/2017 |

OTHER PUBLICATIONS

International Search Report from PCT/KR2017/004832, dated Sep. 18, 2017, 11 pages.

Schwalm, Reinhold, UV Coatings Basics Recent Developments and New Applications, Elsevier Science, Dec. 21, 2006, 3 pages.

Odian George, Principle of Polymerization, Second Edition, 1981, John Wiley & Sons, New York, p. 203, 3 pages.

Extended European Search Report including Written Opinion for Application No. EP17888305.4 dated Mar. 22, 2019.

Third Party Observation for Application No. PCT/KR2017/004832 dated Apr. 17, 2019.

* cited by examiner

SUPER ABSORBENT POLYMER AND METHOD FOR PRODUCING SAME

CROSS-REFERENCE TO RELATED APPLICATION(S)

The present application is a national phase entry under 35 U.S.C. § 371 of International Application No. PCT/KR2017/004832, filed on May 10, 2017, which claims the benefit of Korean Patent Application No. 10-2016-0180348, filed on Dec. 27, 2016 and Korean Patent Application No. 10-2017-0050399, filed on Apr. 19, 2017, the disclosures of which are incorporated herein by reference.

TECHNICAL FIELD

The present invention relates to a super absorbent polymer having excellent absorption performance, and a method for producing the same.

BACKGROUND OF ART

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. In such hygienic materials, the super absorbent polymer is generally contained in a state of being spread in the pulp. In recent years, however, continuous efforts have been made to provide hygienic materials such as diapers having a thinner thickness. As a part of such efforts, the development of so-called pulpless diapers and the like in which the content of pulp is reduced or pulp is not used at all is being actively advanced.

As described above, in the case of hygienic materials in which the pulp content is reduced or the pulp is not used, a super absorbent polymer is contained at a relatively high ratio and these super absorbent polymer particles are inevitably contained in multiple layers in the hygienic materials. In order for the whole super absorbent polymer particles contained in the multiple layers to absorb liquid such as urine more efficiently, not only the super absorbent polymer needs to basically exhibit high absorption performance and absorption rate, but also it needs to exhibit more improved liquid permeability. That is, the super absorbent polymer should exhibit more improved liquid permeability, so the super absorbent polymer particles of the surface layer which first comes in contact with the liquid such as urine are absorbed and allow to absorb and pass the remaining liquid quickly. It becomes possible to absorb such remaining liquid effectively and quickly by the super absorbent polymer particles of the subsequent layer.

Accordingly, recently, various attempts have been made to develop more improved super absorbent polymer, but these technical requirements are not sufficiently satisfied yet.

DETAILED DESCRIPTION OF THE INVENTION

Technical Problem

It is one object of the present invention to provide a super absorbent polymer having excellent absorption performance, and a method for producing the same.

Technical Solution

In order to achieve the above objects, the present invention provides a super absorbent polymer as follows:

the super absorbent polymer comprising:

a base polymer powder comprising a first cross-linked polymer of a water-soluble ethylenically unsaturated monomer having at least partially neutralized acidic groups; and a surface cross-linked layer formed on the base polymer powder and comprising a second cross-linked polymer in which the first cross-linked polymer is further cross-linked via a surface crosslinking agent, wherein the super absorbent polymer has:

a 15-min gel-AUL at 0.3 psi of 13 g/g or more, an absorbency under load (AUL) of 18 g/g or more, a gel bed permeability (GBP) of 30 darcy or more, and a vortex time of 45 seconds or less as measured according to the measurement method of Vortex.

The present invention also provides a super absorbent polymer as follows:

the super absorbent polymer comprising:

a base polymer powder comprising a first cross-linked polymer of a water-soluble ethylenically unsaturated monomer having at least partially neutralized acidic groups; and a surface cross-linked layer formed on the base polymer powder and comprising a second cross-linked polymer in which the first cross-linked polymer is further cross-linked via a surface crosslinking agent, wherein the super absorbent polymer has:

a 15-min gel-AUL at 0.3 psi of 13 g/g or more, a gel bed permeability (GBP) of 30 darcy or more, and a vortex time of 45 seconds or less as measured according to the measurement method of Vortex.

In order to improve the absorption performance of the super absorbent polymer, a method of increasing the surface area of the super absorbent polymer has been studied. In order to widen the surface area of the super absorbent polymer, a method of using a foaming agent during polymerization of a water-soluble ethylenically unsaturated monomer is known, but use of an excessive foaming agent may cause problems in distribution and storage because the gel strength of the super absorbent polymer is lowered or the density is lowered. As another method, there is a method of reducing the particle size through coarse pulverization of the hydrogel polymer, but when an excessive shearing force is applied during the coarse pulverization, there is a problem that the physical properties of the super absorbent polymer are deteriorated or the process of coarse pulverization is difficult.

Thus, according to the present invention, by using a surfactant together with a foaming agent during the polymerization of the water-soluble ethylenically unsaturated monomer as described later, it is possible to prevent the gel strength from being lowered and the density from being lowered by uniform forming. In addition, due to the surfactant during coarse pulverization of the hydrogel polymer, it is pulverized to be smaller than the particle size usually produced, thereby improving the absorption performance of the super absorbent polymer as a final product.

Hereinafter, embodiments of the present invention will be described in more detail.

Super Absorbent Resin

The water-soluble ethylenically unsaturated monomer constituting the first cross-linked polymer may be any monomer commonly used in the production of a super absorbent polymer. As a non-limiting example, the water-soluble ethylenically unsaturated monomer may be a compound represented by the following Chemical Formula 1:

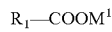  [Chemical Formula 1]

in Chemical Formula 1, $R_1$ is an alkyl group having 2 to 5 carbon atoms containing an unsaturated bond, and $M^1$ is a hydrogen atom, a monovalent or divalent metal, an ammonium group or an organic amine salt.

Preferably, the above-described monomer may be at least one selected from the group consisting of acrylic acid, methacrylic acid, and a monovalent metal salt, a divalent metal salt, an ammonium salt, and an organic amine salt thereof. When acrylic acid or a salt thereof is used as the water-soluble ethylenically unsaturated monomer, it is advantageous in that a super absorbent polymer having improved absorption property can be obtained. In addition, as the monomer, maleic anhydride, fumaric acid, crotonic acid, itaconic acid, 2-acryloylethanesulfonic acid, 2-methacryloylethanesulfonic acid, 2-(meth)acryloylpropane suffonic acid, or 2-(meth)acrylamido-2-methylpropane sulfonic acid, (meth)acrylamide, N-substituted (meth)acrylate, 2-hydroxyethyl(meth)acrylate, 2-hydroxypropyl(meth)acrylate, methoxypolyethylene glycol(meth)acrylate, polyethylene glycol (meth)acrylate, (N,N)-dimethylaminoethyl(meth)acrylate, (N,N)-dimethylaminopropyl(meth)acrylamide, and the like may be used.

Here, the water-soluble ethylenically unsaturated monomers may have an acidic group, wherein at least a part of the acidic group may be neutralized. Preferably, the monomers may be those partially neutralized with an alkali substance such as sodium hydroxide, potassium hydroxide, ammonium hydroxide, or the like. In this case, a degree of neutralization of the monomer may be 40 to 95 mol %, or 40 to 80 mol %, or 45 to 75 mol %. The range of the degree of neutralization may vary depending on the final physical properties. An excessively high degree of neutralization causes the neutralized monomers to be precipitated, and thus polymerization may not readily occur, whereas an excessively low degree of neutralization not only greatly deteriorates the absorbency of the polymer, but also endows the polymer with hard-to-handle properties, such as those of an elastic rubber.

The second cross-linked polymer is obtained by additionally crosslinking the surface of the base resin powder via a surface crosslinking agent. The surface crosslinking agent and the surface crosslinking method will be described later.

Meanwhile, the super absorbent polymer according to the present invention has a 15-min gel-AUL at 0.3 psi of 13 g/g or more. The 15-min gel-AUL at 0.3 psi refers to the amount of a physiological saline solution (0.9 wt % NaCl) which is absorbed by a super absorbent polymer under a load of 0.3 psi for 15 minutes after 0.16 g of a super absorbent polymer is primarily swollen in 1.5 g of physiological saline solution under no load. This means the ability of a super absorbent polymer to absorb a large amount of water continuously and rapidly under a load of 0.3 psi after the super absorbent polymer is primarily swollen under no load. The concrete measurement method thereof will be further specified in the following embodiments.

Preferably, the super absorbent polymer according to the present invention has a 15-min gel-AUL at 0.3 psi of 13.5 g/g or more, 14.0 g/g or more, 14.5 g/g or more, or 15.0 g/g or more. In addition, the higher the value of the 15-min gel-AUL, it is more excellent. Thus, there is no practical upper limit, but as an example, it is 25.0 g/g or less, 24.0 g/g or less, 23.0 g/g or less, 22.0 g/g or less, 21.0 g/g or less, or 20.0 g/g or less.

Further, the super absorbent polymer according to the present invention has a 15-min gel-AUL at 0.6 psi of 12 g/g or more. The 15-min gel-AUL at 0.6 psi is the same as the 15-min gel-AUL at 0.3 psi previously described, but it is measured under load of 0.6 psi instead of 0.3 psi. In addition, the higher the value of the 15-min gel-AUL, it is more excellent. Thus, there is no practical upper limit, but as an example, it is 25.0 g/g or less, 24.0 g/g or less, 23.0 g/g or less, 22.0 g/g or less, 21.0 g/g or less, or 20.0 g/g or less.

Further, the super absorbent polymer according to the present invention has an AUL of 18 g/g or more. The AUL means the amount of a saline solution absorbed under a load of 0.9 psi for 1 hour, which means the total amount of water which the superabsorbent resin can absorb. The concrete measurement method thereof will be further specified in the following embodiments.

Preferably, the AUL is 18.1 g/g or more, 18.2 g/g or more, 18.3 g/g or more, 18.4 g/g or more, or 18.5 g/g or more. In addition, the higher the value of the AUL, it is more excellent. Thus, there is no practical upper limit, but as an example, it is 25.0 g/g or less, 24.0 g/g or less, 23.0 g/g or less, 22.0 g/g or less, 21.0 g/g or less, or 20.0 g/g or less.

Further, the super absorbent polymer according to the present invention has a gel bed permeability (GBP) of 30 darcy or more. The GBP means a fluidity of water absorbed by the super absorbent polymer, which means the ability to rapidly transfer water absorbed by the super absorbent polymer to another super absorbent polymer. The concrete measurement method thereof will be further specified in the following embodiments.

Preferably, the GBP is 35 darcy or more, 40 darcy or more, or 45 darcy or more. Further, the upper limit of the GBP is 65 darcy or less, 60 darcy or less, or 55 darcy or less.

Further, the super absorbent polymer according to the present invention has a vortex time of 45 seconds or less as measured according to the measurement method of Vortex. The vortex time (absorption rate) means a time during which the vortex of the liquid disappears due to rapid absorption when the super absorbent polymer is added to the physiological saline solution and stirred. This can define a rapid water absorption capacity of the super absorbent polymer. The concrete measurement method thereof will be more specified in the following embodiments. Further, the lower limit of the vortex time is, for example, 26 seconds or more, 27 seconds or more, or 28 seconds or more.

Further, the super absorbent polymer according to the present invention has a centrifuge retention capacity (CRC) for a physiological saline solution (0.9 wt % sodium chloride aqueous solution) for 30 minutes of 29 g/g or more. The centrifuge retention capacity means the ability to retain water absorbed by the super absorbent polymer as it is. The concrete measurement method thereof will be further specified in the following embodiments.

Preferably, the centrifuge retention capacity is 29.5 g/g or more, 30.0 g/g or more, or 30.5 g/g or more, and 35 g/g or less, 34 g/g or less, or 33 g/g or less.

Further, preferably, the super absorbent polymer according to the present invention has an average particle diameter of 300 to 600 μm. Also preferably, in the super absorbent polymer according to the present invention, a super absorbent polymer having a particle diameter of 300 to 600 μm is contained in an amount of 45 to 85% by weight. Further, preferably, in the super absorbent polymer, a super absorbent polymer having a particle diameter of 300 μm or less is contained in an amount of 15% by weight or more.

Method for Producing Super Absorbent Polymer

The present invention provides a method for producing a super absorbent polymer comprising the following steps:

the method for producing a super absorbent polymer comprising the steps of:

crosslinking a water-soluble ethylenically unsaturated monomer having at least partially neutralized acidic groups in the presence of an internal crosslinking agent, a foaming agent and a surfactant to form a hydrogel polymer containing a first crosslinked polymer (step 1);

coarsely pulverizing the hydrogel polymer to prepare a hydrogel polymer having an average particle diameter of 1.0 mm to 2.0 mm (step 2);

drying and pulverizing the hydrogel polymer to form a base polymer power (step 3); and heat-treating and surface-crosslinking the base polymer powder in the presence of a surface crosslinking agent to form a super absorbent polymer particle (step 4).

Hereinafter, the above preparation method will be described in detail for each step.

(Step 1)

Step 1 is a step of forming a hydrogel polymer which is a step of crosslinking an internal crosslinking agent, a foaming agent, a surfactant, and a monomer composition comprising a water-soluble ethylenically unsaturated monomer having at least partially neutralized acidic groups.

In this case, the water-soluble ethylenically unsaturated monomer is as described above. Further, the concentration of the water-soluble ethylenically unsaturated monomer in the monomer composition may be appropriately adjusted in consideration of the polymerization time, the reaction conditions and the like, and it may be preferably 20 to 90% by weight, or 40 to 65% by weight. These concentration ranges may be advantageous for adjusting the pulverization efficiency during pulverization of the polymer described below, without needing to remove unreacted monomers after polymerization by using the phenomenon of gel effect occurring in the polymerization reaction of the highly concentrated aqueous solution. However, when the concentration of the monomer is excessively low, the yield of the super absorbent polymer can be lowered. Conversely, when the concentration of the monomer is excessively high, it may arise problems in the processes, for example, a part of the monomer may be precipitated, or the pulverization efficiency may be lowered during pulverization of the polymerized hydrogel polymer, etc., and the physical properties of the super absorbent polymer may be deteriorated.

Further, as the internal crosslinking agent, any compound can be used without particular limitation as long as it enables introduction of a crosslink bond upon polymerization of the water-soluble ethylenically unsaturated monomer. Non-limiting examples of the internal crosslinking agent may include multifunctional crosslinking agents, such as N,N'-methylenebisacrylamide, trimethylolpropane tri(meth)acrylate, ethylene glycol di(meth)acrylate, polyethylene glycol (meth)acrylate, propylene glycol di(meth)acrylate, polypropylene glycol(meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, pentaerythritol tetraacrylate, triarylamine, ethylene glycol diglycidyl ether, propylene glycol, glycerin, or ethylene carbonate, which may be used alone or in combination of two or more thereof, but are not limited thereto.

Such internal crosslinking agent may be added at a concentration of about 0.001 to 1% by weight, based on the monomer composition. That is, if the concentration of the internal crosslinking agent is too low, the absorption rate of the polymer is lowered and the gel strength may become weak, which is undesirable. Conversely, if the concentration of the internal crosslinking agent is too high, the absorption capacity of the polymer is lowered and thereby is not preferred for an absorbent.

Further, in step 1, a polymerization initiator generally used in the production of a super absorbent polymer can be included. As a non-limiting example, as the polymerization initiator, a thermal polymerization initiator, a photo-polymerization initiator or the like may be used depending on the polymerization method. In particular, the thermal polymerization initiator can be used. However, even in the case of the photo-polymerization method, a certain amount of heat is generated by ultraviolet irradiation or the like, and a certain amount of heat is generated in accordance with the progress of the polymerization reaction, which is an exothermic reaction, and thus, a thermal polymerization initiator may further be included.

As the thermal polymerization initiator, one or more compounds selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like. In addition, examples of the azo-based initiator may include 2,2-azobis(2-amidinopropane)dihydrochloride, 2,2-azobis-(N, N-dimethylene)isobutyramidine dihydrochloride, 2-(2-(carbamoylazo)isobutylonitril, 2,2-azobis[2-(2-imidazolin-2-yl)propane]dihydrochloride, 4,4-azobis-(4-cyanovaleric acid), and the like. More various thermal polymerization initiators are well disclosed in "Principle of Polymerization" written by Odian, (Wiley, 1981), p 203, the content of which is incorporated herein by reference.

The photo-polymerization initiator used herein may include, for example, one or more compounds selected from the group consisting of benzoin ether, dialkyl acetophenone, hydroxyl alkylketone, phenyl glyoxylate, benzyl dimethyl ketal, acyl phosphine and α-aminoketone. Among them, as a specific example of the acylphosphine, a commonly used lucyrin TPO, that is, 2,4,6-trimethyl-benzoyl-trimethyl phosphine oxide may be used. More various photo-polymerization initiators are well disclosed in "UV Coatings: Basics, Recent Developments and New Application" written by Reinhold Schwalm, (Elsevier, 2007), p 115, the content of which is incorporated herein by reference.

The polymerization initiator may be added in a concentration of about 0.001 to 1% by weight based on the monomer composition. That is, when the concentration of the polymerization initiator is too low, the polymerization rate may become slow and a large amount of residual monomer may be extracted in the final product, which is not preferable. Conversely, when the concentration of the polymerization initiator is higher than the above range, the polymer chains constituting the network become short, and thus the extractable content is increased and physical properties of the polymer may deteriorate such as a reduction in absorbency under load, which is not preferable.

Further, the monomer composition includes a foaming agent. The foaming agent acts to increase the surface area by causing foaming during polymerization to produce pores in the hydrogel polymer. As the foaming agent, a carbonate can be used. As an example, sodium bicarbonate, sodium carbonate, potassium bicarbonate, potassium carbonate, calcium bicarbonate, calcium carbonate, magnesiumbicarbonate or magnesium carbonate can be used.

Further, the foaming agent is preferably used in an amount of 1500 ppmw or less based on the weight of the water-soluble ethylenically unsaturated monomer. When the amount of the foaming agent used is more than 1500 ppmw, the pores become too large, the gel strength of the super absorbent polymer lowers and the density becomes low, which may cause problems in distribution and storage. Further, the foaming agent is preferably used in an amount of 500 ppmw or more, or 1000 ppmw or more, based on the weight of the water-soluble ethylenically unsaturated monomer.

In addition, the monomer composition includes a surfactant. The surfactant allows to induce uniform dispersion of the foaming agent to perform a uniform foaming when foaming, thereby preventing the gel strength from being lowered or the density being lowered. Moreover, in step 2, which will be described later, pulverization is performed to be a size smaller than the particle size usually produced due to the surfactant during coarse pulverization of the hydrogel polymer, thereby improving the absorption performance of the super absorbent resin as the final product.

As the surfactant, it is preferable to use an anionic surfactant. Specifically, the surfactant includes $SO_3$ anion, and a compound represented by the following Chemical Formula 2 can be used.

   [Chemical Formula 2]

in Chemical Formula 2,

R is an alkyl having 8 to 16 carbon atoms.

Further, the surfactant is preferably used in an amount of 300 ppmw or less based on the weight of the water-soluble ethylenically unsaturated monomer. When the amount of the surfactant used exceeds 300 ppmw, the content of the surfactant in the super absorbent polymer increases, which is not preferable. Further, the surfactant is preferably used in an amount of 100 ppmw or more, or 150 ppmw or more, based on the weight of the water-soluble ethylenically unsaturated monomer.

In addition, the monomer composition may further include additives such as a thickener, a plasticizer, a preservation stabilizer, an antioxidant, etc., if necessary.

Further, such a monomer composition can be prepared in the form of a solution in which a raw material such as the above-mentioned monomer is dissolved in a solvent. In this case, any usable solvent can be used without limitation in the constitution as long as it can dissolve the above-mentioned raw material. Examples of the solvent may include water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, N,N-dimethylacetamide, or a mixture thereof.

Further, the formation of the hydrogel polymer through polymerization of the monomer composition may be performed by a general polymerization method, and the process is not particularly limited. As a non-limiting example, the polymerization method are largely classified into a thermal polymerization and a photo-polymerization according to the type of the polymerization energy source, and the thermal polymerization may be carried out in a reactor like a kneader equipped with agitating spindles and the photo-polymerization may be carried out in a reactor equipped with a movable conveyor belt.

As an example, the monomer composition is injected into a reactor like a kneader equipped with the agitating spindles, and thermal polymerization is performed by providing hot air thereto or heating the reactor, thereby obtaining the hydrogel polymer. In this case, the hydrogel polymer, which is discharged from the outlet of the reactor according to the type of agitating spindles equipped in the reactor, may be obtained as particles with a size of centimeters or millimeters. Specifically, the hydrogel polymer may be obtained in various forms according to the concentration of the monomer composition injected thereto, the injection speed, or the like, and the hydrogel polymer having a (weight average) particle diameter of 2 to 50 mm may be generally obtained.

As another example, when the photo-polymerization of the monomer composition is performed in a reactor equipped with a movable conveyor belt, a sheet-shaped hydrogel polymer may be obtained. In this case, the thickness of the sheet may vary depending on the concentration of the monomer composition injected thereto and the injection speed, and the polymer sheet is preferably controlled to have typically a thickness of 0.5 to 5 cm in order to secure the production speed or the like while enabling a uniform polymerization of the entire sheet.

In this case, the hydrogel polymer obtained by the above-mentioned method may have a water content of 40 to 80% by weight. Meanwhile, the "water content" as used herein means a weight occupied by moisture with respect to a total weight of the hydrogel polymer, which may be the value obtained by subtracting the weight of the dried polymer from the weight of the hydrogel polymer. Specifically, the water content can be defined as a value calculated by measuring the weight loss due to evaporation of moisture in the polymer in the drying process by raising the temperature of the polymer through infrared heating. At this time, the drying conditions may be determined as follows: the drying temperature is increased from room temperature to about 180° C. and then the temperature may be maintained at 180° C., and the total drying time may be set to 20 minutes, comprising 5 minutes for the temperature rising step.

(Step 2)

Step 2 is a step of coarsely pulverizing the hydrogel polymer prepared in step 1 to prepare a hydrogel polymer having a small average particle diameter.

In particular, as described above, in the present invention, as a surfactant is used in the production of the hydrogel polymer, the hydrogel polymer can be pulverized into a particle diameter of 1.0 mm to 2.0 mm which is smaller than the particle diameter which is usually produced. In order to pulverize the hydrogel polymer into the above-mentioned particle diameter as in the present invention without using a surfactant, an excessive shearing force is required, which is difficult in the process, and the physical properties of the super absorbent polymer are deteriorated. However, as the present invention uses a surfactant, pulverization can be made into a smaller particle diameter, and thereby, the surface area of the super absorbent polymer is widened and excellent absorption capacity can be exhibited.

A pulverizing machine used herein may include, but its configuration is not limited to, for example, any one selected from the group consisting of a vertical pulverizer, a turbo cutter, a turbo grinder, a rotary cutter mill, a cutter mill, a disc mill, a shred crusher, a crusher, a chopper, and a disc cutter. However, it is not limited to the above-described examples.

Further, for the efficiency of the coarse pulverization, the coarse pulverization can be performed plural times depending on the size of the particle diameter. For example, the hydrogel polymer is subjected to the first coarse pulverization into an average particle of about 10 mm, which can be again subjected to the second coarse pulverization into an average particle of about 5 mm, followed by the third coarse pulverization into the above-mentioned average particle.

(Step 3)

Step 3 is a step of drying and pulverizing the hydrogel polymer prepared in step 2 to prepare a surface crosslinking described later.

The drying temperature may be 50 to 250° C. When the drying temperature is less than 50° C., it is likely that the drying time becomes too long or the physical properties of the super absorbent polymer finally formed is deteriorated. When the drying temperature is higher than 250° C., only the surface of the polymer is excessively dried, and thus fine powder may be generated and the physical properties of the super absorbent polymer finally formed may be deteriorated. The drying may be preferably carried out at a temperature of 150° C. to 200° C., and more preferably at a temperature of 160° C. to 190° C. Meanwhile, the drying time may be 20 minutes to 15 hours, in consideration of the process efficiency and the like, but it is not limited thereto.

In the drying step, any drying method may be selected and used without limitation in the constitution if it is a method commonly used in the relevant art. Specifically, the drying step may be carried out by a method such as hot air supply, infrared irradiation, microwave irradiation or ultraviolet irradiation. When the drying step as above is finished, the water content of the polymer may be 0.05 to 10% by weight.

Next, a step of pulverizing the dried polymer obtained through such a drying step is carried out.

The polymer powder obtained through the pulverizing step may have a particle diameter of 150 μm to 850 μm. Specific examples of a pulverizing device that can be used to pulverize into the above particle diameter may include a ball mill, a pin mill, a hammer mill, a screw mill, a roll mill, a disc mill, a jog mill or the like, but it is not limited to the above-described examples.

Further, in order to control the physical properties of the super absorbent polymer powder finally commercialized after the pulverization step, a separate step of classifying the polymer powder obtained after the pulverization depending on the particle diameter may be undergone. Preferably, a polymer having a particle diameter of 150 μm to 850 μm is classified and only the polymer powder having such a particle diameter is subjected to the surface crosslinking reaction described later and finally commercialized.

(Step 4)

Step 4 is a step of crosslinking the surface of the base resin polymer prepared in step 3, which is a step of heat-treating and surface-crosslinking the base polymer powder in the presence of a surface crosslinking solution containing a surface crosslinking agent to form a super absorbent polymer particle.

Here, the kind of the surface crosslinking agent contained in the surface crosslinking solution is not particularly limited. As a non-limiting example, the surface crosslinking agent may be at least one compound selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene carbonate, ethylene glycol, diethylene glycol, propylene glycol, triethylene glycol, tetraethylene glycol, propanediol, dipropylene glycol, polypropylene glycol, glycerin, polyglycerin, butanediol, heptanediol, hexanediol trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this case, the content of the surface crosslinking agent may be properly controlled according to the type of the surface crosslinking agent or reaction conditions, and preferably, the content may be controlled to 0.001 to 5 parts by weight based on 100 parts by weight of the base polymer. If the content of the surface crosslinking agent is too low, surface modification may not be properly performed to deteriorate physical properties of the final super absorbent polymer. On the contrary, if the surface crosslinking agent is excessively used, excessive surface crosslinking reaction may occur, leading to deterioration in absorption capability of the super absorbent polymer, which is not preferable.

In addition, the surface crosslinking solution may further include at least one solvent selected from the group consisting of water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide. The solvent may be included in an amount of 0.5 to 10 parts by weight based on 100 parts by weight of the base polymer.

In addition, the surface crosslinking solution may further include a thickener. If the surface of the base polymer powder is further crosslinked in the presence of the thickener, it is possible to minimize the deterioration of the physical properties even after the pulverization. Specifically, as the thickener, at least one selected from a polysaccharide and a hydroxy-containing polymer may be used. The polysaccharide may be a gum type thickener, a cellulose type thickener and the like.

Specific examples of the gum type thickener include xanthan gum, arabic gum, karaya gum, tragacanth gum, ghatti gum, guar gum, locust bean gum, and psyllium seed gum. Specific examples of the cellulose type thickener include hydroxypropylmethyl cellulose, carboxymethyl cellulose, methylcellulose, hydroxymethyl cellulose, hydroxyethyl cellulose, hydroxypropyl cellulose, hydroxyethylmethyl cellulose, hydroxymethylpropyl cellulose, hydroxyethylhydroxypropyl cellulose, ethylhydroxyethyl cellulose, and methylhydroxypropyl cellulose. Meanwhile, specific examples of the hydroxy-containing polymer include polyethylene glycol, polyvinyl alcohol and the like.

Meanwhile, in order to perform the surface crosslinking, a method of placing the surface crosslinking solution and the base polymer into a reaction tank and mixing them, a method of spraying a surface crosslinking solution onto the base polymer, a method in which the base polymer and the surface crosslinking solution are continuously supplied in a continuously operating mixer and mixed, or the like can be used.

In addition, the surface crosslinking may be carried out at a temperature of 100 to 250° C., and may be continuously performed after the drying and pulverizing step proceeding at a relatively high temperature. At this time, the surface crosslinking reaction may be carried out for 1 to 120 minutes, or 1 to 100 minutes, or 10 to 60 minutes. That is, in order to prevent a reduction in physical properties due to damages of the polymer particles by excessive reaction while inducing the minimal surface crosslinking reaction, the surface modification step may be performed under the above-described conditions.

Advantageous Effects

As described above, the super absorbent polymer according to the present invention exhibits excellent absorption performance and is preferably used for hygienic materials such as diapers, and thus can exhibit excellent performance.

DETAILED DESCRIPTION OF THE EMBODIMENTS

Hereinafter, preferred examples are provided for better understanding of the invention. However, these Examples are given for illustrative purposes only and are not intended to limit the scope of the present invention thereto.

Example 1

(Step 1)

A solution (solution A) in which 9 g of 0.5% IRGACURE 819 initiator (80 ppmw based on the monomer composition) diluted with acrylic acid and 40 g of 5% polyethylene glycol diacrylate (PEGDA, Mw=400) diluted with acrylic acid were mixed was prepared. Then, a solution (solution B) in which 2.1 g of 5% allyl methacrylate diluted with acrylic acid was mixed was prepared.

490 g of acrylic acid, the solution A and the solution B were injected into a 2 L glass reactor surrounded by a jacket through which a heat medium pre-cooled at 25° C. was circulated. Then, 850 g of 24% caustic soda solution (solution C) was slowly added dropwise to the glass reactor and mixed. After confirming that the temperature of the mixture increased to about 72° C. or higher by neutralization heat, the mixed solution was left until it was cooled. The degree of neutralization of acrylic acid in the mixed solution thus obtained was about 70 mol %. 5 g of 2% sodium dodecylsulfate solution (solution D-1) diluted with water was prepared as a surfactant. Further, 20 g of 4% sodium bicarbonate solution (solution D-2) diluted with water and 30 g of 4% sodium persulfate solution (solution E) diluted with water were prepared. Then, when the mixed solution was cooled to about 45° C., the solutions D-1, D-2 and E previously prepared were injected into the mixed solution and mixed.

(Step 2)

Then, the mixed solution prepared in step 1 was poured in a Vat-type tray (15 cm in width×15 cm in length) installed in a square polymerizer which had a light irradiation device installed at the top and whose inside was preheated to 80° C. Subsequently, the mixed solution was irradiated with light. It was confirmed that a gel was formed on the surface after about 20 seconds from light irradiation, and it was confirmed that polymerization reaction occurred simultaneously with foaming after about 30 seconds from light irradiation. Then, the polymerization reaction was performed for additional 2 minutes, and the polymerized sheet was taken out and cut into a size of 3 cm×3 cm. Then, the cut sheet was subjected to a chopping process using a meat chopper to prepare crumbs. The average particle diameter of the prepared crumbs was 1.5 mm.

(Step 3)

Then, the crumbs prepared in step 2 were dried in an oven capable of shifting airflow up and down. The crumbs were uniformly dried by flowing hot air at 180° C. from the bottom to the top for 15 minutes and from the top to the bottom for 15 minutes, so that the dried product had a water content of about 2% or less. The dried crumbs were pulverized using a pulverizer and classified to obtain a base polymer having a particle diameter of 150 to 850 μm. The base polymer thus prepared had a centrifuge retention capacity of 35.4 g/g. The centrifuge retention capacity was measured according to Experimental Example described below.

(Step 4)

Thereafter, 100 g of the base polymer prepared in step 3 was mixed with a crosslinking agent solution obtained by mixing 4 g of water, 1 g of ethylene carbonate, and 0.1 g of Aerosil 200 (Evonik), and then surface crosslinking reaction was carried out at 190° C. for 30 minutes. The resultant product was pulverized and sieved to obtain a surface-crosslinked super absorbent polymer having a particle diameter of 150 to 850 μm. 0.1 g of Aerosil 200 was dry-added to the obtained super absorbent polymer and mixed in a dry state to prepare a super absorbent polymer.

Example 2

(Step 1)

A mixed solution was prepared in the same manner as in step 1 of Example 1, except that 1.3 g of the solution B (solution in which 2.1 g of 5% allyl methacrylate diluted with acrylic acid was mixed) was used and 30 g of the solution D-2 (4% sodium bicarbonate solution diluted with water) was used.

(Step 2)

Then, the mixed solution prepared in step 1 was poured in a Vat-type tray (15 cm in width×15 cm in length) installed in a square polymerizer which had a light irradiation device installed at the top and whose inside was preheated to 80° C. Subsequently, the mixed solution was irradiated with light. It was confirmed that a gel was formed on the surface after about 20 seconds from light irradiation, and it was confirmed that polymerization reaction occurred simultaneously with foaming after about 30 seconds from light irradiation. Then, the polymerization reaction was performed for additional 2 minutes, and the polymerized sheet was taken out and cut into a size of 3 cm×3 cm. Then, the cut sheet was subjected to a chopping process using a meat chopper to prepare crumbs. The average particle diameter of the prepared crumbs was 1.7 mm.

(Step 3)

Then, the crumbs prepared in step 2 were dried in an oven capable of shifting airflow up and down. The crumbs were uniformly dried by flowing hot air at 180° C. from the bottom to the top for 15 minutes and from the top to the bottom for 15 minutes, so that the dried product had a water content of about 2% or less. The dried crumbs were pulverized using a pulverizer and classified to obtain a base polymer having a particle diameter of 150 to 850 μm. The base polymer thus prepared had a centrifuge retention capacity of 36.1 g/g. The centrifuge retention capacity was measured according to Experimental Example described below.

(Step 4)

Thereafter, 100 g of the base polymer prepared in step 3 was mixed with a crosslinking agent solution obtained by mixing 4 g of water, 1 g of ethylene carbonate, 1 g of propylene carbonate and 0.1 g of Aerosil 200 (Evonik), and then surface crosslinking reaction was carried out at 190° C. for 30 minutes. The resultant product was pulverized and sieved to obtain a surface-crosslinked super absorbent polymer having a particle diameter of 150 to 850 μm. 0.1 g of alumina powder (Alu 130, Evonik) was dry-added to the obtained super absorbent polymer and mixed in a dry state to prepare a super absorbent polymer.

Example 3

(Step 1)

A mixed solution was prepared in the same manner as in step 1 of Example 1, except that 10 g of the solution D-1 (2% sodium dodecylsulfate solution diluted with water) was used.

(Step 2)

Then, the mixed solution prepared in step 1 was poured in a Vat-type tray (15 cm in width×15 cm in length) installed in a square polymerizer which had a light irradiation device installed at the top and whose inside was preheated to 80° C. Subsequently, the mixed solution was irradiated with light. It was confirmed that a gel was formed on the surface after about 20 seconds from light irradiation, and it was confirmed that polymerization reaction occurred simultaneously with foaming after about 30 seconds from light irradiation. Then, the polymerization reaction was performed for additional 2 minutes, and the polymerized sheet was taken out and cut into a size of 3 cm×3 cm. Then, the cut sheet was subjected to a chopping process using a meat chopper to prepare crumbs. The average particle diameter of the prepared crumbs was 1.2 mm.

(Step 3)

Then, the crumbs prepared in step 2 were dried in an oven capable of shifting airflow up and down. The crumbs were uniformly dried by flowing hot air at 180° C. from the bottom to the top for 15 minutes and from the top to the bottom for 15 minutes, so that the dried product had a water content of about 2% or less. The dried crumbs were pulverized using a pulverizer and classified to obtain a base polymer having a particle diameter of 150 to 850 μm. The base polymer thus prepared had a centrifuge retention capacity of 34.2 g/g. The centrifuge retention capacity was measured according to Experimental Example described below.

(Step 4)

Thereafter, 100 g of the base polymer prepared in step 3 was mixed with a crosslinking agent solution obtained by mixing 4 g of water, 1 g of ethylene carbonate and 0.1 g of alumina powder (Alu 130, Evonik), and then surface crosslinking reaction was carried out at 190° C. for 30 minutes. The resultant product was pulverized and sieved to obtain a surface-crosslinked super absorbent polymer having a particle diameter of 150 to 850 μm. 0.1 g of alumina powder (Alu 130, Evonik) was dry-added to the obtained super absorbent polymer and mixed in a dry state to prepare a super absorbent polymer.

Comparative Example 1

A solution (solution A) in which 9 g of 0.5% IRGACURE 819 initiator (80 ppmw based on the monomer composition) diluted with acrylic acid and 19 g of 5% polyethylene glycol diacrylate (PEGDA, Mw=400) diluted with acrylic acid were mixed was prepared. Then, 13 g of a solution (solution B) of 5% trimethylolpropane triacrylate containing 9 mol % of ethylene oxide (Ethoxylated-TMPTA, TMP(EO)9TA, M-3190 manufactured by Miwon Specialty Chemical Co., Ltd.) diluted with acrylic acid was prepared.

470 g of acrylic acid, the solution A and the solution B were injected into a 2 L glass reactor surrounded by a jacket through which a heat medium pre-cooled at 25° C. was circulated. Then, 850 g of 24% caustic soda solution (solution C) was slowly added dropwise to the glass reactor and mixed. After confirming that the temperature of the mixture increased to about 72° C. or higher by neutralization heat, the mixed solution was left until it was cooled. The degree of neutralization of acrylic acid in the mixed solution thus obtained was about 70 mol %. 30 g of 4% sodium persulfate solution (solution E) diluted with water were prepared. Then, when the mixed solution was cooled to about 45° C., the solution E previously prepared was injected into the mixed solution and mixed.

Then, the polymerization and chopping processes were carried out in the same manner as in Example 1. The average particle diameter of the prepared crumbs was 3.4 mm. Then, the drying and pulverizing processes were carried out in the same manner as in Example 1. The base polymer thus prepared had a centrifuge retention capacity of 36.4 g/g. The centrifuge retention capacity was measured according to Experimental Example described below. Then, the surface crosslinking and after-treatment were carried out in the same manner as in Example 1 to obtain a super absorbent polymer.

Comparative Example 2

A solution (solution A) in which 11 g of 0.5% IRGACURE 819 initiator (80 ppmw based on the monomer composition) diluted with acrylic acid and 36 g of 5% polyethylene glycol diacrylate (PEGDA, Mw=400) diluted with acrylic acid were mixed was prepared.

480 g of acrylic acid and the solution A were injected into a 2 L glass reactor surrounded by a jacket through which a heat medium pre-cooled at 25° C. was circulated. Then, 850 g of 24% caustic soda solution (solution C) was slowly added dropwise to the glass reactor and mixed. After confirming that the temperature of the mixture increased to about 72° C. or higher by neutralization heat, the mixed solution was left until it was cooled. The degree of neutralization of acrylic acid in the mixed solution thus obtained was about 70 mol %. 30 g of 4% sodium persulfate solution (solution E) diluted with water were prepared. Then, when the mixed solution was cooled to about 45° C., the solution E previously prepared was injected into the mixed solution and mixed.

Then, the polymerization and chopping processes were carried out in the same manner as in Example 1. The average particle diameter of the prepared crumbs was 3.8 mm. Then, the drying and pulverizing processes were carried out in the same manner as in Example 1. The base polymer thus prepared had a centrifuge retention capacity of 39.7 g/g. The centrifuge retention capacity was measured according to Experimental Example described below. Then, the surface crosslinking and after-treatment were carried out in the same manner as in Example 1 to obtain a super absorbent polymer.

Comparative Example 3

A solution (solution A) in which 11 g of 0.5% IRGACURE 819 initiator (80 ppmw based on the monomer composition) diluted with acrylic acid and 42 g of 5% polyethylene glycol diacrylate (PEGDA, Mw=400) diluted with acrylic acid were mixed was prepared.

470 g of acrylic acid and the solution A were injected into a 2 L glass reactor surrounded by a jacket through which a heat medium pre-cooled at 25° C. was circulated. Then, 850 g of 24% caustic soda solution (solution C) was slowly added dropwise to the glass reactor and mixed. After confirming that the temperature of the mixture increased to about 72° C. or higher by neutralization heat, the mixed solution was left until it was cooled. The degree of neutralization of acrylic acid in the mixed solution thus obtained was about 70 mol %. 1.8 g of 1% Sugar ester (S-1670) (solution D-3) diluted with acrylic acid was prepared as a surfactant. Further, 15 g of 4% sodium bicarbonate solution (solution DA-4) diluted with water and 30 g of 4% sodium persulfate solution (solution E) diluted with water were prepared. Then, when the mixed solution was cooled to about 45° C., the solutions D-3, D-4 and E previously prepared were injected into the mixed solution and mixed.

Then, the polymerization and chopping processes were carried out in the same manner as in Example 1. The average particle diameter of the prepared crumbs was 2.8 mm. Then, the drying and pulverizing processes were carried out in the same manner as in Example 1. The base polymer thus prepared had a centrifuge retention capacity of 38.4 g/g. The centrifuge retention capacity was measured according to Experimental Example described below. Then, the surface crosslinking and after-treatment were carried out in the same manner as in Example 1 to obtain a super absorbent polymer.

Comparative Example 4

A solution (solution A) in which 11 g of 0.5% IRGA-CURE 819 initiator (80 ppmw based on the monomer composition) diluted with acrylic acid and 32 g of 5% polyethylene glycol diacrylate (PEGDA, Mw=400) diluted with acrylic acid were mixed was prepared.

470 g of acrylic acid and the solution A were injected into a 2 L glass reactor surrounded by a jacket through which a heat medium pre-cooled at 25° C. was circulated. Then, 850 g of 24% caustic soda solution (solution C) was slowly added dropwise to the glass reactor and mixed. After confirming that the temperature of the mixture increased to about 72° C. or higher by neutralization heat, the mixed solution was left until it was cooled. The degree of neutralization of acrylic acid in the mixed solution thus obtained was about 70 mol %. 2.1 g of 1% Sugar ester (S-1670) (solution D-5) diluted with acrylic acid was prepared as a surfactant. Further, 30 g of 4% sodium persulfate solution (solution E) diluted with water were prepared. Then, when the mixed solution was cooled to about 45° C., the solutions D-3 and E previously prepared were injected into the mixed solution and mixed.

Then, the polymerization and chopping processes were carried out in the same manner as in Example 1. The average particle diameter of the prepared crumbs was 4.4 mm. Then, the drying and pulverizing processes were carried out in the same manner as in Example 1. The base polymer thus prepared had a centrifuge retention capacity of 44.5 g/g. The centrifuge retention capacity was measured according to Experimental Example described below. Then, the surface crosslinking and after-treatment were carried out in the same manner as in Example 1 to obtain a super absorbent polymer.

Comparative Example 5

For comparison, a product (product name: IM-930), produced and sold commercially by Sandia, was used as Comparative Example 5.

Experimental Example: Evaluation of Physical Properties of Super Absorbent Polymer The physical properties of the super absorbent polymer prepared in Examples and Comparative Examples were evaluated by the following methods, and the results are shown in Table 1 below.

(1) Absorbency Under Load (AUL)

The absorbency under load (AUL) at 0.9 psi for a physiological saline solution was measured for each super absorbent polymer prepared in Examples and Comparative Examples according to EDANA (European Disposables and Nonwovens Association) recommended test method No. WSP 242.2. Among the super absorbent polymers to be measured, super absorbent polymers which was passed through a US standard 30 mesh screen and retained on a US standard 50 mesh screen, were selectively classified to obtain the super absorbent polymers having a particle size of 300 μm to 600 μm, and the AUL thereof was measured.

Specifically, a 400 mesh metal made of stainless steel was installed at the bottom of a plastic cylinder having an inner diameter of 25 mm. $W_0$ (g, about 0.16 g) of a super absorbent polymer for measuring the absorbency under load were uniformly scattered on the screen at room temperature and relative humidity of 50%. Then, a piston capable of uniformly providing a load of 6.3 kPa (0.9 psi) was put thereon. At this time, the piston used was designed so that the outer diameter was slightly smaller than 25 mm and thus it could move freely up and down without any gap with the inner wall of the cylinder. Then, the weight $W_1(g)$ of the device thus prepared was measured.

A glass filter having a diameter of 90 mm and a thickness of 5 mm was put inside a Petri dish having the diameter of 150 mm, and then 0.9 wt % of a physiological saline solution was poured in the Petri dish. At this time, the physiological saline solution was poured until the surface level became equal to the upper surface of the glass filter. Then, a sheet of filter paper having a diameter of 90 mm was put on the glass filter.

Subsequently, the prepared device was placed on the filter paper so that the super absorbent polymer in the device was swelled by a physiological saline solution under load. After one hour, the weight $W_2(g)$ of the device containing the swollen super absorbent polymer was measured.

Using the weight thus measured, the absorbency under load was calculated according to the following Mathematical Formula 1.

$$AUP(g/g)=[W_2(g)-W_1(g)]/W_0(g) \quad \text{[Mathematical Formula 1]}$$

in Mathematical Formula 1, $W_0(g)$ is an initial weight (g) of the super absorbent polymer, $W_1(g)$ is the total sum of a weight of the super absorbent polymer and a weight of the device capable of providing a load to the super absorbent polymer, and $W_2(g)$ is the total sum of a weight of the super absorbent polymer and a weight of the device capable of providing a load to the super absorbent polymer, after absorbing a physiological saline solution to the super absorbent polymer under a load (0.9 psi) for 1 hour.

(2) Gel-AUL

The Gel-AUL at 0.3 psi was measured using the same device as that used in the '(1) Absorbency under load (AUL)'. Among the super absorbent polymers to be measured, super absorbent polymers which was passed through a US standard 30 mesh screen and retained on a US standard 50 mesh screen, were selectively classified to obtain the super absorbent polymers having a particle size of 300 µm to 600 µm, and the Gel-AUL thereof was measured.

Specifically, the resin $W_0$ (g, 0.16 g) obtained in Examples and Comparative Examples was put into an AUL kit used in the '(1) Absorbency under load (AUL)', and a piston capable of providing a load of 0.3 psi was put thereon. Then, the weight $W_3$ (g) of the device thus prepared was measured. Subsequently, the piston was removed, and the super absorbent polymer was immersed in 1.5 g of physiological saline solution under no load to perform a primary swelling. Then, the physiological saline solution was absorbed under a load of 0.3 psi for 15 minutes and then subjected to a vacuum desorption under a vacuum pressure of 5 psi for 30 seconds to remove a physiological saline solution existing between gels. The weight $W_4$ (g) of AUL kit including the physiological saline solution wholly containing gel therein was measured.

Using the respective weights thus obtained, the 15-min Gel-AUL at 0.3 psi was calculated according to the following Mathematical Formula 2.

$$\text{15-min gel-}AUL \text{ at 0.3 psi(g/g)} = [W_4(g) - W_3(g)]/W_0(g) \quad \text{[Mathematical Formula 2]}$$

in Mathematical Formula 2, $W_0(g)$ is an initial weight (0.16 g) of the super absorbent polymer, $W_3(g)$ is the total sum (g) of an initial weight of the super absorbent polymer and a weight of the device capable of providing a load of 0.3 psi to the super absorbent polymer, and $W_4(g)$ is the total sum (g) of a weight of the super absorbent polymer and a weight of the device capable of providing a load of 0.3 psi to the super absorbent polymer, after absorbing 1.5 g of a physiological saline solution to the super absorbent polymer under no load to perform a primary swelling, absorbing the physiological saline solution under a load of 0.3 psi for 15 minutes and then subjecting to vacuum desorption under a vacuum pressure of 5 psi for 30 seconds.

In addition, the gel-AUL at 0.6 psi was measured in the same manner as described above, except that a load of 0.3 psi was changed to 0.6 psi.

(3) Centrifuge Retention Capacity (CRC)

The centrifuge retention capacity (CRC) by water absorption capacity under a non-loading condition was measured for the super absorbent polymers of Examples and Comparative Examples in accordance with EDANA (European Disposables and Nonwovens Association) recommended test method No. WSP 241.3. Among the super absorbent polymers to be measured, super absorbent polymers which was passed through a US standard 30 mesh screen and retained on a US standard 50 mesh screen, were selectively classified to obtain the super absorbent polymers having a particle size of 300 µm to 600 µm, and the CRC thereof was measured.

Specifically, $W_0$ (g, about 0.2 g) of the super absorbent polymers of Examples and Comparative Examples were uniformly put in a nonwoven fabric-made bag, followed by sealing. Then, the bag was immersed in a physiological saline solution composed of 0.9 wt % aqueous sodium chloride solution at room temperature. After 30 minutes, water was removed from the bag by centrifugation at 250 G for 3 minutes, and the weight $W_6(g)$ of the bag was then measured. Further, the same procedure was carried out without using the super absorbent polymer, and then the resultant weight $W_5(g)$ was measured.

Using the respective weights thus obtained, CRC (g/g) was calculated according to the following Mathematical Formula 3.

$$\text{CRC(g/g)} = \{[W_6(g) - W_5(g) - W_0(g)]/W_0(g)\} \quad \text{[Mathematical Formula 3]}$$

in Mathematical Formula 3, $W_0(g)$ is an initial weight (g) of the super absorbent polymer, $W_5(g)$ is the weight of the device not including the super absorbent polymer, measured after immersing and absorbing the device into a physiological saline solution for 30 minutes and then dehydrating the same by using a centrifuge at 250 G for 3 minutes, and $W_6(g)$ is the weight of the device including the super absorbent polymer, measured after immersing and absorbing the super absorbent polymer into a physiological saline solution at room temperature for 30 minutes and then dehydrating the same by using a centrifuge at 250 G for 3 minutes.

(4) Gel Bed Permeability (GBP)

The free swell Gel Bed Permeability (GBP) for a physiological saline solution was measured for each super absorbent polymer prepared in Examples and Comparative Examples according to the following method described in Korean Patent Application No. 10-2014-7018005.

Specifically, the apparatus shown in FIGS. 1 to 3 was used to measure the free swell GBP. First, the plunger 536 installed with the weight 548 was placed in an empty sample container 530, and the height from the top of the weight 548 to the bottom of the sample container 530 was measured to an accuracy of 0.01 mm using an appropriate gauge. The force to which the thickness gauge applied during the measurement was adjusted to less than about 0.74 N.

Meanwhile, among the super absorbent polymers for measuring GBP, super absorbent polymers which was passed through a US standard 30 mesh screen and retained on a US standard 50 mesh screen, were selectively classified to obtain the super absorbent polymers having a particle size of 300 µm to 600 µm.

About 2.0 g of the super absorbent polymer classified in this way was placed in the sample container 530 and spread out evenly on the bottom of the sample container. Then, the container not containing the plunger 536 and the weight 548 therein, was submerged in 0.9 wt % physiological saline solution for about 60 minutes and allowed the super absorbent polymer to swell under no load condition. At this time, the sample container 530 was placed on the mesh located in a liquid reservoir so that the sample container 530 was raised slightly above the bottom of the liquid reservoir. As the mesh, those which did not affect the movement of the physiological saline solution into the sample container 530 were used. During saturation, the height of the physiological saline solution was allowed to be adjusted such that the surface within the sample container was defined by the swollen super absorbent polymer, rather than the physiological saline solution.

At the end of this period, the assembly of the plunger 536 and weight 548 was placed on the swollen super absorbent polymer 568 in the sample container 530 and then the sample container 530, plunger 536, weight 548 and swollen super absorbent polymer 568 were removed from the solution. Thereafter, before GBP measurement, the sample container 530, plunger 536, weight 548 and swollen super absorbent polymer 568 were placed on a flat, large grid non-deformable plate of uniform thickness for about 30 seconds. The height from the top of the weight 548 to the bottom of the sample container 530 was measured again by using the same thickness gauge as previously used. Then, the height measurement value of the device in which the plunger 536 equipped with the weight 548 was placed in the empty sample container 530 was subtracted from the height measurement value of the device including the swollen super absorbent polymer 568, thereby obtaining the thickness or height "H" of the swollen super absorbent polymer.

For the GBP measurement, 0.9 wt % physiological saline solution was flowed into the sample container 530 containing the swollen super absorbent polymer 568, the plunger 536 and the weight 548. The flow rate of a physiological saline solution into the sample container 530 was adjusted to cause the physiological saline solution to overflow the top of the cylinder 534, thereby resulting in a consistent head pressure equal to the height of the sample container 530. Then, the quantity of solution passing through the swollen super absorbent polymer 568 versus time was measured gravimetrically using the scale 602 and beaker 603. Data points from the scale 602 were collected every second for at least sixty seconds once the overflow has started. The flow rate (Q) passing through the swollen super absorbent polymer 568 was determined in units of grams/second (g/s) by a linear least-square fit of fluid passing through the sample 568 (in grams) versus time (in seconds).

Using the data thus obtained, the GBP (cm$^2$) was calculated according to the following Mathematical Formula 4.

$$K=[Q \times H \times \mu]/[A \times \rho \times P]$$ [Mathematical Formula 4]

in Mathematical Formula 4
K is a gel bed permeability (cm$^2$),
Q is a flow rate (g/sec),
H is a height of swollen super absorbent polymer (cm),
μ is a liquid viscosity (poise) (about 1 cP for the physiological saline solution used with this Test),
A is a cross-sectional area for liquid flow (28.27 cm$^2$ for the sample container used with this Test),
ρ is a liquid density (g/cm$^3$) (about 1 g/cm$^3$, for the physiological saline solution used with this Test), and
P is a hydrostatic pressure (dynes/cm$^2$) (normally about 7,797 dyne/cm$^2$).

The hydrostatic pressure was calculated from P=ρ×g×h, where ρ is a liquid density (g/cm$^3$), g is a gravitational acceleration (nominally 981 cm/sec$^2$), and h is a fluid height (for example, 7.95 cm for the GBP Test described herein).

At least two samples were tested and the results were averaged to determine the free swell GBP of the super absorbent polymer, and the unit was converted to darcy (1 darcy=0.98692×10$^{-8}$ UW) and shown in Table 1 below.

(5) Absorption Rate (Vortex Time)
The absorption rate of the super absorbent polymers prepared in Examples and Comparative Examples was measured in second unit according to the method described in International Publication WO1987/003208.

Specifically, the absorption rate (vortex time) was calculated by a process in which 2 g of the super absorbent polymer was added to 50 mL of physiological saline solution at 23° C. to 24° C., and stirred at 600 rpm by a magnetic stirring bar (diameter 8 mm, length 31.8 mm), and the time required for the vortex to disappear was determined in second unit.

The above measurement results are shown in Table 1 below.

TABLE 1

| | Gel-AUL (g/g) | | CRC | AUL | GBP | Vortex |
|---|---|---|---|---|---|---|
| | 0.3 psi | 0.6 psi | (g/g) | (g/g) | (darcy) | (sec) |
| Ex. 1 | 15.2 | 12.3 | 31 | 18.5 | 50 | 43 |
| Ex. 2 | 18.5 | 14.1 | 30.5 | 19.3 | 62 | 41 |
| Ex. 3 | 19.1 | 15.4 | 30 | 19.7 | 48 | 36 |
| Comparative Ex. 1 | 13.8 | 11.3 | 31.5 | 19 | 55 | 85 |
| Comparative Ex. 2 | 12.3 | 9.3 | 34 | 15 | 25 | 85 |
| Comparative Ex. 3 | 14.8 | 6.9 | 34 | 11 | 25 | 35 |
| Comparative Ex. 4 | 12.6 | 8.8 | 37 | 12 | 15 | 90 |
| Comparative Ex. 5 | 14.6 | 10.8 | 30 | 16 | 30 | 30 |

The invention claimed is:

1. A super absorbent polymer comprising:
a base polymer powder comprising a first cross-linked polymer of a water-soluble ethylenically unsaturated monomer having at least partially neutralized acidic groups, wherein the first cross-linked polymer is prepared by crosslinking the water-soluble ethylenically unsaturated monomer in the presence of an internal crosslinking agent, a foaming agent and a surfactant, wherein the surfactant is sodium dodecylsulfate; and
a surface cross-linked layer formed on the base polymer powder and comprising a second cross-linked polymer in which the first cross-linked polymer is further cross-linked via a surface crosslinking agent,
wherein the super absorbent polymer has:
a 15-min gel-AUL at 0.3 psi of 13 g/g or more,
an absorbency under load (AUL) of 18 g/g or more,
a gel bed permeability (GBP) of 30 darcy or more, and
a vortex time of 45 seconds or less, wherein the vortex time means the amount of time required until the vortex disappears after adding 2 g of a super absorbent polymer to 50 mL of physiological saline solution and then stirring the mixture at 600 rpm.

2. The super absorbent polymer of claim 1, wherein the super absorbent polymer has a 15-min gel-AUL at 0.6 psi of 12 g/g or more.

3. The super absorbent polymer of claim 1, wherein the super absorbent polymer has a centrifuge retention capacity (CRC) of 29 g/g or more.

4. The super absorbent polymer of claim 1, wherein the super absorbent polymer has an average particle diameter of 300 μm to 600 μm.

5. The super absorbent polymer of claim 1, wherein in the super absorbent polymer, a super absorbent polymer having a particle diameter of 300 μm to 600 μm is contained in an amount of 45 to 85% by weight.

6. A method for producing a super absorbent polymer, comprising the steps of:
crosslinking a water-soluble ethylenically unsaturated monomer having at least partially neutralized acidic groups in the presence of an internal crosslinking agent, a foaming agent and a surfactant to form a hydrogel polymer containing a first cross-linked polymer, wherein the surfactant is sodium dodecylsulfate;
coarsely pulverizing the hydrogel polymer to prepare a hydrogel polymer having an average particle diameter of 1.0 mm to 2.0 mm;
drying and pulverizing the hydrogel polymer to form a base polymer powder; and
heat-treating and surface-crosslinking the base polymer powder in the presence of a surface crosslinking agent to form a surface cross-linked layer on the base polymer powder, wherein the surface cross-linked layer comprises a second cross-linked polymer in which the first cross-linked polymer is further cross-linked via the surface crosslinking agent, wherein the superabsorbent polymer comprises:

the base polymer powder comprising the first cross-linked polymer of the water-soluble ethylenically unsaturated monomer having at least partially neutralized acidic groups; and the surface cross-linked layer formed on the base polymer powder, wherein the super absorbent polymer has:

a 15-min gel-AUL at 0.3 psi of 13 g/g or more, a gel bed permeability (GBP) of 30 darcy or more, and a vortex time of 45 seconds or less, wherein the vortex time means the amount of time required until the vortex disappears after adding 2 g of a super absorbent polymer to 50 mL of physiological saline solution and then stirring the mixture at 600 rpm.

7. The method for producing a super absorbent polymer of claim 6, wherein the foaming agent is sodium bicarbonate, sodium carbonate, potassium bicarbonate, potassium carbonate, calcium bicarbonate, calcium carbonate, magnesium bicarbonate, or magnesium carbonate.

8. The method for producing a super absorbent polymer of claim 7, wherein the foaming agent is used in an amount of 1500 ppmw or less based on the weight of the water-soluble ethylenically unsaturated monomer.

9. The method for producing a super absorbent polymer of claim 6, wherein the surfactant is used in an amount of 300 ppmw or less based on the weight of the water-soluble ethylenically unsaturated monomer.

10. A super absorbent polymer comprising:

a base polymer powder comprising a first cross-linked polymer of a water-soluble ethylenically unsaturated monomer having at least partially neutralized acidic groups, wherein the first cross-linked polymer is prepared by crosslinking the water-soluble ethylenically unsaturated monomer in the presence of an internal crosslinking agent, a foaming agent and a surfactant, wherein the surfactant is sodium dodecylsulfate; and a surface cross-linked layer formed on the base polymer powder and comprising a second cross-linked polymer in which the first cross-linked polymer is further cross-linked via a surface crosslinking agent, wherein the super absorbent polymer has:

a 15-min gel-AUL at 0.3 psi of 13 g/g or more, a gel bed permeability (GBP) of 30 darcy or more, and a vortex time of 45 seconds or less, wherein the vortex time means the amount of time required until the vortex disappears after adding 2 g of a super absorbent polymer to 50 mL of physiological saline solution and then stirring the mixture at 600 rpm.

* * * * *